United States Patent
Dahl

[11] Patent Number: 5,911,958
[45] Date of Patent: Jun. 15, 1999

[54] MULTITUBE FALLING FILM REACTOR FOR THE CONTINUOUS MANUFACTURING OF SULFONATED AND/OR SULFATED COMPOUNDS

[76] Inventor: Birger Dahl, Villaveien 1, Sarpsborg, Norway

[21] Appl. No.: 08/930,415
[22] PCT Filed: Mar. 22, 1996
[86] PCT No.: PCT/NO96/00065
    § 371 Date: Sep. 29, 1997
    § 102(e) Date: Sep. 29, 1997
[87] PCT Pub. No.: WO96/30117
    PCT Pub. Date: Oct. 3, 1996
[51] Int. Cl.⁶ .................................................. B01J 8/06
[52] U.S. Cl. ............................................ 422/197; 422/202
[58] Field of Search ...................................... 422/197, 196, 422/202

[56] References Cited

U.S. PATENT DOCUMENTS 4,886,089 12/1989 Gabrlik et al. .
5,445,801 8/1995 Pisoni .

FOREIGN PATENT DOCUMENTS 570 844 of 0000 European Pat. Off. .

*Primary Examiner*—Timothy McMahon
*Attorney, Agent, or Firm*—Christensen O'Connor Johnson Kindness PLLC

[57] ABSTRACT

Multitube falling film reactor (MTR) for continuous manufacturing of sulfonated and/or sulfated products using gaseous, diluted sulfur trioxide, ($SO_{3(dil)}$) to produce surface active agents or simply surfactants, useful in the cosmetic and detergent industry. Each individual nozzle-set comprises a male part (19) and the other half (45) on the male part (10). The male part (10) forms together with the female part (19), an annular slot (21) with a constant and under all operational conditions well defined length (47), which together with a fixed opening/width determines the individual pressure drop of the said slot and thereby the individual organic flow. With this arrangement, completely homogenous distribution of organic feed is achieved without the necessity of calibration.

5 Claims, 3 Drawing Sheets

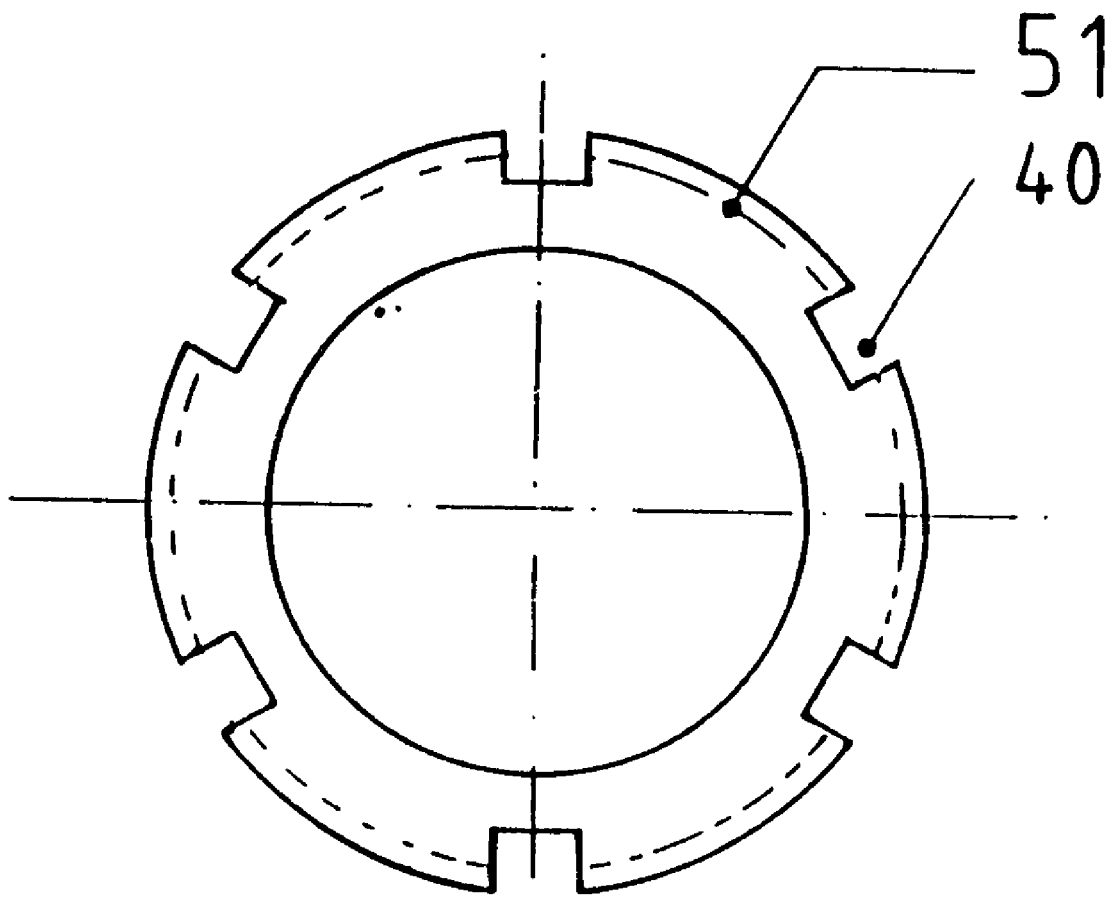
Fig. 3  SNITT A-A

MULTITUBE FALLING FILM REACTOR FOR THE CONTINUOUS MANUFACTURING OF SULFONATED AND/OR SULFATED COMPOUNDS

This application is the U.S. national stage application of International application Ser. No. PCT/NO/00065, filed Mar. 22, 1996, which is a continuation of Norwegian application Ser. No. 95.1178, filed Mar. 28, 1995, and claims the benefit of the filing dates thereof under 35 U.S.C. §119.

BACKGROUND OF THE INVENTION

Multitube falling film reactors represent today a well established technology, and is frequently the preferred reactorprinciple for sulphonation and sulphation reactions, both giving advanced products; surfactants for the cosmetic and detergent industry. The reactors are assembled according to conventional principles for a multitube shell and tube heat-exchanger with different baffle-arrangements and cooling liquids, with water as the dominating cooling liquid. Typical for all reactors are separate chambers for diluted gas, organic compound, cooling liquid and collection of finished products, chambers mentioned from top of reactor to bottom outlet.

When producing surfactants for the said industry, the gaseous and diluted reactant is sulfur trioxide, typical organic compounds are liquids at 15° C. or higher, the main variety of raw-material being alkylates, fatty alcohols, etoxilated fatty alcohols, alpha-olefins and methyl-esters. Any chemical compound equipped with a socalled flexible hydrogen atom might be sulphonated or sulphated. (Sulphated for all compounds where hydrogen is linked to an oxygen atom, sulphonated for the linkage hydrogen-carbon.)

The overall chemical reactions taking place, are characterized by the fact that diluted, gaseous $SO_3$ is a very aggressive/reactive reactant, and that the reactions are all extremely rapid and exothermic. Altogether, these properties challenge the control of the molar ratio between the reactants, and only with the very best control of both total and local molar ratio, the best products are achieved. Any deviation in the molar ratio will unavoidably result in increased quantity of undesired by-products, and the main product will suffer from bad colour, lower active matter content, higher content of sulphates, higher content of nonsulphated/-sulphonated organic compounds and consequently lower yield with a higher raw-material consumption. In a MTR, where the numbers of individual and parallel reactor-element could be from two to more than hundred, the most important parameter is the local molar ratio between the reactants, and therefore the best possible and most homogeneous distribution of organic compound to each individual reactor-element. Even the smallest deviation in local molar ratio, can not be fully compensated for later in the process.

To avoid any misunderstanding, total molar ratio is defined as the ratio between the total number of moles $SO_3$ fed to the reactor divided by the total number of moles organic compound fed to the same reactor. By advanced dosing system for liquid sulfur/liquid sulfur dioxide/liquid sulfur trioxide and finally organic compounds, the total molar ratio can be kept almost constant and without any significant impact on the final product properties.

The local molar ratio, defined the same way but between local flows of said reactants for each individual nozzle-element, is predominantly depending on an even and homogeneous feed, kg/hour of organic reactant to each individual nozzle-set from one common, organic chamber, since a gas carrying a far lower viscosity has a higher tendency of even distribution according to the principle of "the way of lowest resistance". The nozzle-set construction will therefore appear as the decisive and critical element for individual organic flow and local molar ratio. In a MTR, all the nozzle-sets are fed from one common, organic chamber. The nozzle-construction also allows a reactor to consist of only one reactor element, where the total molar ratio becomes equal and identical to the local molar ratio, accuracy only depending on the external dosing system.

Of great and vital importance is also an even and homogeneous distribution of the organic film formed circumferentially on the internal, surface of the female part. This can be achieved, provided that the film distribution/formation on the internal surface of the said female part is determined by the same accuracy as the dosing/metering of organic compounds of the nozzle-set for all reactor elements. It means altogether that the film-formation should be determined by the same accuracy as the dosing/metering of organic compounds, i.e. a well defined annular slot in respect of length an width for all known, operational conditions.

There are several, different concepts of constructions available on the market and already patented, relevant in this connection are following patents:

U.S. Pat. No. 3,918,917 Nitto Chemical Industry Co., Ltd.
U.S. Pat. No. 4,183,897 Construzioni Meccaniche G. Mazzoni S.p.A
FR 2,449,665 Ballestra Chimica S.p.A
EP 0,570,844 A1 Meccaniche Moderne S.r.l These patents and constructional concepts can be described and grouped by following:

precalibrated and selected/grouped orifices (materials totally different from this patent), characterized by a relatively long distance between the zone for metering/dosing and the zone for film formation. (Pre-selected/grouped orifices should not be mixed up with the terminology nozzle-set and nozzle-set construction described in this document.)

conical or cylindrical slots where even a lower accuracy (compared to this invention) of organic feed only can be achieved through a mechanical adjustment of the slots length or opening by shims. If the slot opening and slot length were well defined in these constructions, and besides appeared with the accuracy described in mentioned patents, no adjustment by shims would be necessary. It is obvious that the location of the male part relatively to the female part by shims, will be influenced by different pressure working on the main flanges/cylindrical plates(pressures different from the conditions during calibration), by the torque on single bolts for tightening, by sealing material and finally by the distance between the cylindrical plates. The fact that all individual nozzle-sets have to be calibrated before start-up, also clearly demonstrates the unsufficient definition of the opening and length of the slots, resulting in a less homogeneous distribution of the film (different thickness around the wetted periphery) on the internal surface of the female part of the nozzle-set.

The main differences/disadvantages for already known and operative constructions compared to the nozzle-set construction described in this document, can be summarized by following:

higher tendency of air-pockets and thereby partly blocking of organic feed during start-up. (Air-pockets in the space between male and female part of the nozzle-set.)

partly more complex components, less easy to machine.

need for time-consuming calibration both before start-up and after an uncontrolled stop during operation, or after a routine washing/cleaning procedure. The accuracy of this calibration will also be influenced by the fact that normal plant conditions are always different from calibration conditions.

generally lower accuracy for individual organic feed compared to the total average of organic feed for all nozzle-sets in operation.

generally will lower accuracy of metering mean increased variation in film thickness.

tightening arrangement for the male and female part of the nozzle-set will influence the accuracy of individual nozzle-set supply and also said accuracy for neighbouring nozzle-sets.

the neccessity of shims adjustment creates very frequently tendency of increased leakages.

accuracy of metering will strongly depend on the torque applied for tightening the bolts.

the individual supply from each nozzle-set will further also be depending on pressure variations during normal operation, pressures working on the different cylindrical plates and giving different impact depending on the location of the nozzle-set on the said plates.

DESCRIPTION OF THE INVENTION

Summary of the Invention

The nozzle-set represents the most vital component/part of any multitube falling film reactor, and this invention relates mainly to the design, construction and assembling of all the individual components comprising a nozzle-set.

The nozzle-set reported in this document, is characterized by a well defined annular slot having a fixed length and a fixed width under all known operational conditions.

The necessity of complicated and less reliable arrangement for calibration like shims etc is eliminated, and the invented nozzle-set will also give a substantial increase in the homogeneity of the film thickness. There is no need for calibration before start-up, or time-consuming re-calibration after a stop in the plant.

A model of the reactor with more than 30 parallell nozzle-sets in full size have been tested, and by introducing the average flow $x_{av}$, g/min, for all nozzle-sets, all individual flows are covered by the range:

$x_{av} \pm 0.2\%$

An accuracy level like this, has uptil now not been reported, and the reactor with the new nozzle-set will be named the NCN reactor, which means: No Calibration Needed.

The NCN nozzle-set may be installed in all MTR reactors designed for heterogene reactions, even for reactions where for instance reactive particles are present and suspended in an inert liguid, (inert to the gaseous reactant).

ATTACHED FIGURES AND DEFINITIONS/TERMINOLOGY

FIG. 3 is a cross section of FIG. 2 A—A enlarged, and shows in detail the six channels for liquid,organic feed to the expansion chamber.

Nozzle-set: A complete unit comprising a female part, a male part, respective tightening arrangement, tightening bolts and sealing system.

Reactortube: A conventional tube, total length 5–7 m, and fixed to the female part of the nozzle-set. The reactortube represents in this way the zone for the chemical reaction taking place, and transfers heat of reaction to the surrounding and circulating cooling liquid.

Reactor-element: A complete unit having as integral parts one nozzle-set, one reactortube and finally sealing arrangements.

Figure 1:
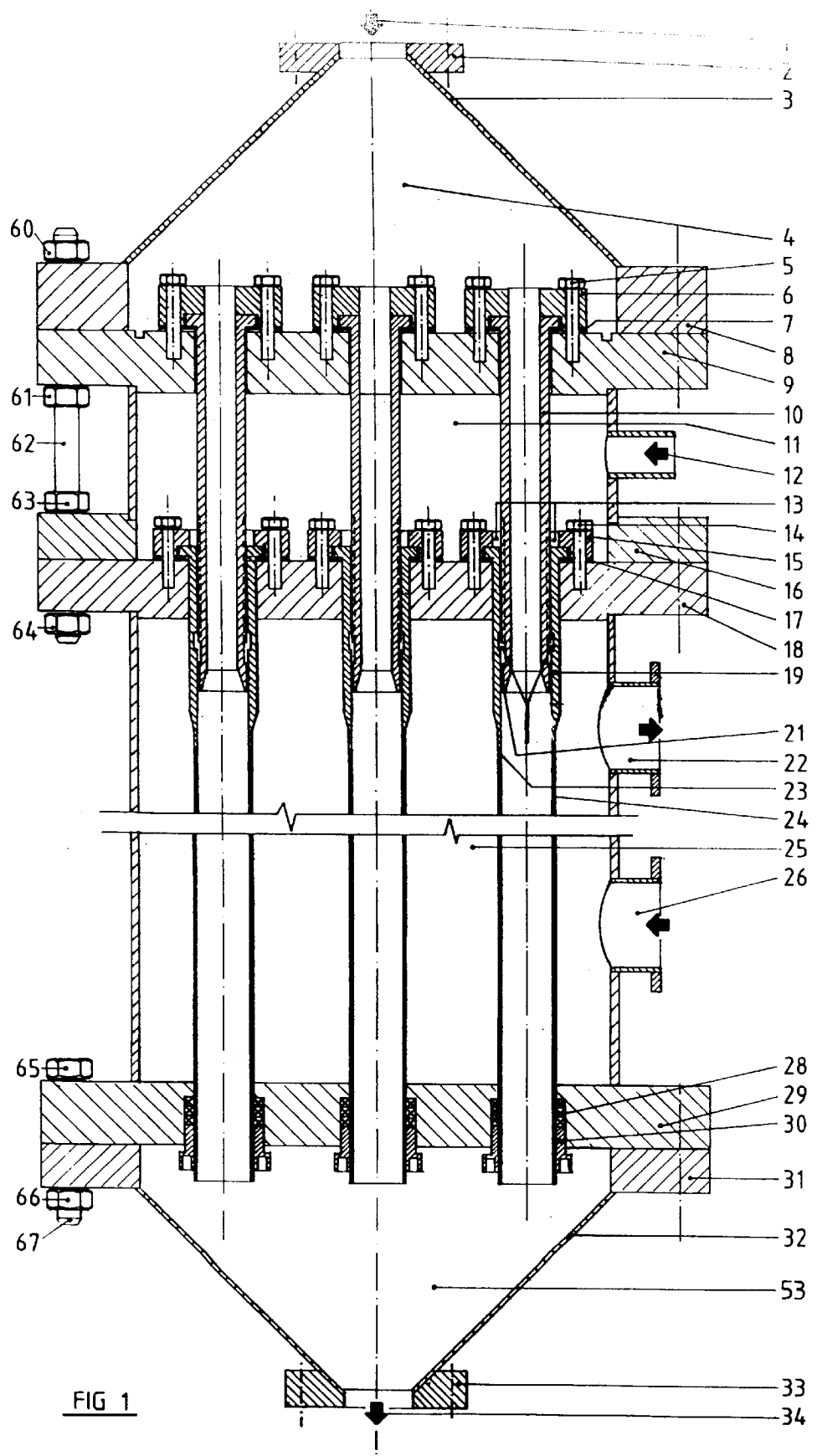
FIG. 1 is a longitudinal section of a complete and assembled multitube falling film reactor Type NCN, with three individual nozzle-sets fixed to reactor-tubes partly in section.

Multitube falling film reactor, FIG. 1: A complete reactor unit including from two to more than hundred reactor-elements together with separate chambers for distribution of gaseous reactant, liquid organic reactant, cooling liquid, collecting chamber for finished product and connections for all material flows.

Reactorhead: Includes the nozzle-sets and the organic chamber defined and limited by a cylindrical plate fixed to a cylindrical spacer fixed to a counter-flange bolted and sealed to the lowest cylindrical plate.

Calibration of nozzle-set: Manual and time-consuming work for all individual nozzle-sets, at least the reactorhead must be fully assembled to accomplish this procedure. A quantity of organic reactant normally corresponding to the nominal capacity of the reactor, is fed to the common organic chamber, and all the individual flows leaving nozzle-sets or reactortubes, are carefully determined by weighing. Based on the measuring results from this procedure, an aritmetic average for the individual flows is calculated, for instance $X_{av}$. Any deviation outside a predetermined and acceptable range, will have to be adjusted for by replacement of the shims having thicknesses different from the ones originally installed. Normally this procedure will have to be repeated uptil several times to reach a range described by:

$X_{av} \pm 1.0\%$

For reactortechnology of yesterday, average ±2.5% is quite usual and rather seldomly average ±1.0% is reached. Unfortunately, the same reactortechnology can neither confirm nor guarantee this range/limit of deviation during normal, operational conditions.

DETAILED DESCRIPTION OF THE INVENTION

Figure 2:
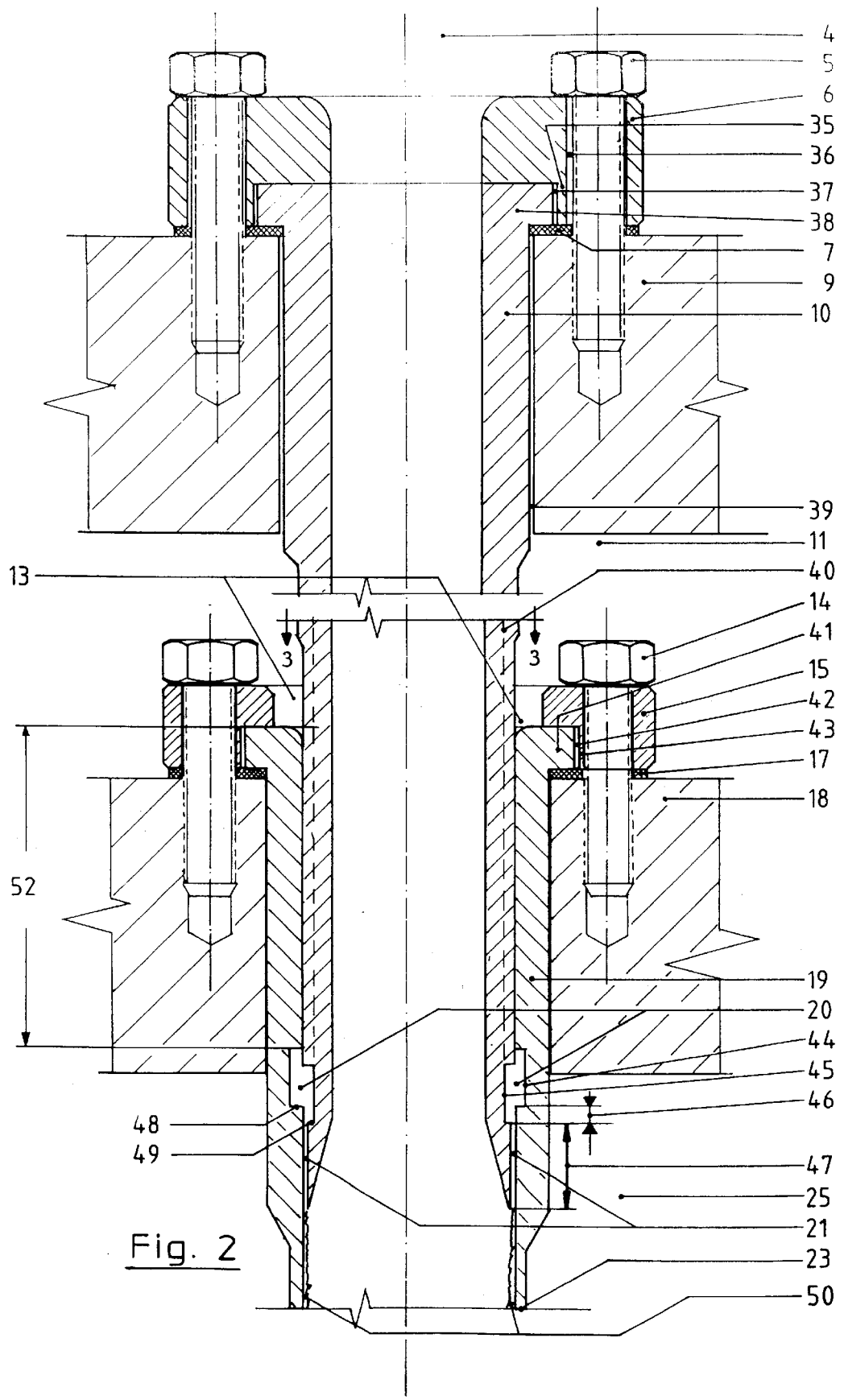
FIG. 2 is a detailed assembly drawing for one complete nozzle-set comprising a female part, a male part, respective tightening arrangement, tightening bolts and sealing system all arrangend on two individual and separated cylindrical plates.

With reference to the attached figures, FIG. 1, FIG. 2 and FIG. 3, together with the definitions and terminology listed in para 3, a complete, multitube falling film reactor vil include more than two reactor-elements in parallell, chamber 4 for distribution of the gaseous reactant, chamber 11 for distribution of organic reactant, chamber 25 for cooling liquid and chamber 53 for collecting of finished product, chamber 53 being defined by plate/flange 29/31 and the conical bottom cap 32, all mentioned parts from reactor top to reactor bottom/outlet. All the chambers are separated from neighbouring chamber with plates/flanges 8, 9, 16, 18, 27, 29 and 31, sealing systems, outer cylindrical mantle and conical caps 3/32 at top and bottom respectively. At the outlet of each reactor-element, stuffing-boxes 28/30 installed in plate 29 efficiently prevent leakage between cooling-chamber 25 and collecting chamber 53. These stuffing boxes allows thermal, longitudinal expansion of reactor-tubes during normal plant conditions/operation.

The upper chamber 4 being fed through 1 and limited by a conical top cap 3 and the upper plate 9 together with the flange 8, evenly distributes the gaseous reactants to all individual reactor-elements.

Liquid, organic reactant being fed from a central pipe-line and distributed to the organic chamber 11 through several feeding-tubes 12. This chamber 11 is also equipped with a on/off ball-valve for de-areation during start-up and operation. The chamber 11 is vented to the surrounding atmosphere. The operating pressure in chamber 11 is given by the pressure drop through the annular slot 21 and the gas pressure in the reactortube 24.

Liquid, organic reactant is fed from the common chamber 11 to each separate nozzle-set at 13 along the total periphery of female part 10 and further to the expansion-chamber 20 through the longitudinal feeding channels FIG. 2/FIG. 3 40. The organic reactant is perfectly metered and distributed through the annular slot 21 forming a continuous and uniform falling film 50 on the internal surface of the female part 19. At the outlet of the slot 21, the liquid organic reactant from chamber 11 meets the gaseous reactant from chamber 4, immediately starting the exothermic and heterogeneous chemical reaction. The heat of the reaction is transferred to the outer surface of the reactor-tube, and continuously removed by the circulating cooling liquid in chamber 25. The cooling liquid fed to the same chamber through 26, leaving at 22. The finished product from all reactor-elements is collected at the bottom of the reactor in chamber 53, leave at 34 and further downstream treated in a special separator/cyclone for the separation of gas/liquid.

The complete nozzle-set will according to this document include a male part 10, a female part 19, tightening arrangements 5/6 and 14/15 respectively, and sealings 7/17 respectively.

Female part 19 equipped with integral tightening flange 41, is fixed to the plate 18 by the tightening ring 15 and two–four bolts 14. The cylindrical plate 18 separates the organic chamber 11 from the cooling chamber 25. The integral flange on female part 19 has an heigth equal to the depth of the tightening-ring 15 at 43, thus forming a completely even surface and together with sealing 17 comprise a sealing system between the female part 19 and the plate 18. Built-in distance/clearance 42 between the said female flange 41 and the said tightening ring 15, efficiently prevents radial forces to occur and acting on the female part 19 through 41.

The position of the female part 19 is according to above only determined by the cylindrical opening in plate 18. Longitudinally, the position is determined by the applied torque on the bolts 14, sealing thickness/compressibility and additionally by different pressure- and temperature-conditions during operation. A cylindrical section/spacer between flange 16 and upper plate 9 forms together with the lower plate 18 the said organic chamber 11. To avoid eccentrisity between plate 9 and 18, plate 18 is equipped with at least two conical guiding pins entering corresponding holes in flange 16 with a high degree of precision.

The female part 19 is internally machined forming one half 44 of the expansion chamber 20. This machined part 44 of the expansion chamber 20 is identical to the other machined half 45 located at the outer surface of the male part 10. Together the two halves comprise the said expansion chamber 20. The female part 19 is fixed to the reactortube 24, length 5–7 m, at 23.

The male part 10 is equipped with a similar, integral flange 38 with the height corresponding to the depth of the tightening ring 6 at 35. Together, flange 38 and ring 6 form a completely even surface and together with sealing at 7 comprises a sealing system between the male part 10 and the plate 9. Built-in distance/clearance 37 between the said male flange 38 and the said tightening ring 6, efficiently prevents radial forces to occur and acting on the male part 10 through 38. The said tightening ring 6 is equipped with oversized holes for bolts. In combination with the said clearance 37, the clearance between the holes in the plate 9 and male part 10, the said oversized holes 36 efficiently prevent any radial forces to occur and act on the said flange 38 nor the total male part 10 of the nozzle-set. The important centering of the male part 10 into the female part 19, is according to above only determined by the guiding zone 52.

Longitudinal channels 40 machined on the outer surface of the male part 10, leeds the organic feed from the chamber 11 to the expansion chamber 20.

The size and number of these channels are carefully selected to give maximum guiding surface in combination with low, lineaer velocity of the liquid making this nozzle-set self-deareating during start-up and operation. Self-deareating as terminology is concequently applied for any gaseous component being present before start-up and/or dispersed gasparticles in the bulk flow of organic that might occur during normal operation. The male part 10 of the said nozzle-set is externally machined to form one half 45 of the expansion chamber 20. Characteristic for this invention and construction is that both the length 47 and the opening of the annular slot 21 is defined once for all and under all known operational conditions, provided that the lower lips 48 and 49 of the halves 44 and 45 respectively under the said conditions always will be separated a distance 46 and with the lip 49 at the lower position. The feed of organic liquid to or from the nozzle-set, will according to this invention only depend on the channel length 47 which is well defined for all nozzle-sets and constant opening of the annular slot 21 formed between the male and female part. The said distance 46 between the said lips 48 and 49, will be determined according to following relation:

The length of half-chambers 44 and/or 45 in expansion-chamber 20 >distance 46>0 The lip 49 always located at the lower position of the two lips 48 and 49

The distance 46 between lip 48 and 49 being normally 2.0–3.0 mm, will permanently and automatically compensate for all sorts of external forces tending to move in longitudinal direction the male part 10 relatively to the female part 19 or opposite.

The pressure drop in the annular slot 21 determines the flow from each nozzle-set, and with the annular slot being constant even when male parts moves relatively to the female part or opposite (limits stated in above relation), the same pressure drop will remain constant and finally thereby the flow.

In other words, for any complete nozzle-set equipped with a constant slot opening 21, the flow will remain constant as long as the distance 46 is within the limits of said relation and thus giving a constant slot length 47 indepent of variations in operational conditions. The nozzle-set will permanently need no mechanical arrangements for adjusting the relative position of male and female part to influence or adjust the individual flows, and there will be no need neither for calibration nor re-calibration.

The invention therefore comprises a multitube falling film reactor with a nozzle-set as described in details above, showing an uptil now unknown accuracy and without the necessity of complicated and less reliable mechanical arrangements for final adjustments of all individual flows. Additionally, any need for calibration before start-up, or re-calibration in connection with uncontrolled stops and routine maintenance, is eliminated compared to other, similar constructions.

The invention has been described according to one embodiment of the invention, and alternatives may be made by one skilled in the art. The invention embraces all such alternatives which are clearly in family to and within the spirit and protective scope of the following claims.

I claim:

1. A multi-tube falling film reactor for the continuous sulphonation and sulphation of a liquid organic substance by reaction with gaseous $SO_3$, comprising: at least two reactor elements, each element consisting of a nozzle set comprising an inner male portion and an outer female portion, which portions are in their respective upper part provided with an integral flange device for mounting to a first chamber plate and a second chamber plate, respectively, the female portion is in its lower part connected to a reactor tube which in its lower part is mounted to a third chamber plate, whereby each reactor element is fed with an organic substance from a common organic chamber through longitudinal channels defined on the outside of the male portion and via an expansion chamber and further down in the reactor tube through an annular channel formed between the outer circular surface of the male portion and inner circular surface of the female portion of the nozzle, the organic substance reacts with the $SO_3$ gas which flows down in the reactor tube through the inner bore of the nozzle from a common gas distribution chamber, the reactor tube and the lower part of the nozzle are further arranged inside a common cooling chamber whereby the resulting product from all reactor elements is collected in a collecting chamber at the bottom of the reactor, wherein the longitudinal channels are extended along the complete contacting/guiding surface between the outer surface of the male portion and the inner surface of the female portion of the nozzle, respectively, characterized in that the expansion chamber is formed as a circumferential groove/milling in the outer circumferential surface of the male portion and that the height of the annular channel between the outer surface of the male portion and the inner surface of the female portion, and thereby the volume of the annular channel itself, is constant with respect to axial displacement of the male portion inside the female portion and thereby every reactor element will maintain a constant flow rate under varying process conditions.

2. Reactor according to claim 1, characterized in that the expansion chamber (20) in the various reactor elements are formed by cooperation between said groove (45) in the outer circumferential surface of the male portion (10) and a circumferential groove/milling (44) in the inner circumferential surface of the female portion (19) of similar volume as the groove (45) in the outer circumferential surface of the male portion (10), the lower circumferential edge (49) of the groove (45) of the male portion (10) during operation having a displacement (46) in relation to and located below the lower circumferential edge (48) of the female portion (19), the displacement (46) is larger than zero and less than the height of each groove (44, 45).

3. The reactor according to claim 1, characterized in that a number of longitudinal channels are six.

4. The reactor according to claim 3, characterized by one of the two reactants being present as gaseous reactant and the other participating reactant present as a liquid at ambient temperature or temperatures corresponding to the reaction conditions, the said reactor assembled as a conventional multitube shell and tube heat exchanger with separated chambers for gaseous reactant, liquid organic reactant, cooling liquid and collection of finished products.

5. The reactor according to 4, characterized by further comprising a plurality of nozzle-sets, from two to more than hundred, and where the said liquid organic reactant is fed to the common organic chamber through a plurality of separated feeding tubes, the organic chamber being defined by cylindrical plates and, counterflange and finally cylindrical spacer fixed and welded to plate and flange, a diluted gaseous reactant is further fed to the common chamber limited by flange, cylindrical plate and conical top cap, and that finished product are collected in chamber defined by a conical cap, cylindrical plate and counterflange, the cylindrical plate equipped with stuffing boxes for reactor tube and arranged at the reactor bottom/outlet.

\* \* \* \* \*

UNITED STATES PATENT AND TRADEMARK OFFICE
CERTIFICATE OF CORRECTION

PATENT NO. : 5,911,958
DATED : June 15, 1999
INVENTOR(S) : B. Dahl

It is certified that error appears in the above-identified patent and that said Letters Patent is hereby corrected as shown below:

| COLUMN | LINE | ERROR |
|---|---|---|
| Pg. 1, col. 1 | Foreign Appl. Priority Data | Before the line beginning with "[51] Int. Cl.$^6$" please insert the following:<br><br>--[30] Foreign Application Priority Data<br>March 28, 1995   Norway . . . . . 95.1178-- |
| 8<br>(Claim 5, line 1) | 30 | "to 4," should read --to claim 4,-- |

Signed and Sealed this

Third Day of October, 2000

Attest:

Q. TODD DICKINSON

*Attesting Officer*          *Director of Patents and Trademarks*